US00PP09191P

United States Patent [19]

McGredy

[11] Patent Number: Plant 9,191

[45] Date of Patent: Jul. 11, 1995

[54] SHRUB ROSE PLANT NAMES 'MACORANLEM'

[75] Inventor: Sam McGredy, Auckland, New Zealand

[73] Assignee: Weeks Wholesale Rose Grower, Inc., Upland, Calif.

[21] Appl. No.: 200,824

[22] Filed: Feb. 23, 1994

[51] Int. Cl.[6] ..... A01H 5/00

[52] U.S. Cl. ..... Plt./1

[58] Field of Search ..... Plt. 1, 11, 22, 13

*Primary Examiner*—Howard J. Locker

*Attorney, Agent, or Firm*—Christie, Parker & Hale

[57] ABSTRACT

A new variety of shrub rose suitable for garden decoration, having flowers of striped orange and yellow coloration.

1 Drawing Sheet

BACKGROUND OF THE INVENTION

This invention relates to a new and distinct variety of shrub rose. The varietal denomination of the new variety is 'Macoranlem'. The plant is an upright to somewhat spreading seedling cultivated for outdoor garden decoration. 'Macoranlem' has as its seed parent the variety known as 'Macnewye' (U.S. Plant Pat. No. 5,428) and as its pollen parent an unnamed seedling of my creation.

SUMMARY OF THE INENTION

Among the features which distinguish the new variety 'Macoranlem' from other presently available and known commercial rose cultivars are the following combination of characteristics: dark new foliage that holds its pigmentation for an unusually long period, striped flowers with unusual coloration of bright orange and yellow, and large glossy foliage with a high degree of powdery mildew resistance. 'Macoranlem' may be propagated by cuttings, budding, grafting, layering and tissue culture.

Asexual propagation of the new variety by budding, grafting and propagation of vegetative cuttings as performed in Kern County and Upland, Calif., shows that the foregoing and other distinguishing characteristics come true to form and are established and transmitted through succeeding propagations.

COMPARISON WITH PARENT VARIETIES

The new rose may be distinguished from its seed parent, 'Macnewye', by the following combination of characteristics: whereas the new cultivar bears flowers of an unusual orange and yellow striped combination, 'Macnewye' bears flowers with a more stable and even coloration of bright orange. The seed parent bears flowers with 20 to 25 petals, whereas 'Macoranlem' bears flowers of significantly fuller petalage (32 to 38). The new cultivar is classified as a Shrub with a somewhat spreading habit, whereas 'Macnewye' is classified as a Grandiflora and has a significantly more upright habit.

The new variety may be distinguished from its pollen parent by the following combination of characteristics: whereas the pollen parent bears flowers with a striped coloration of salmon and red, 'Macoranlem' bears flowers with a striped coloration of bright orange and yellow. The pollen parent bears clusters of small flowers with semi-double petalage, whereas the new cultivar bears significantly larger flowers of much fuller petalage. 'Macoranlem' has large glossy dark foliage, whereas the pollen parent has significantly smaller grey-green foliage with a matte finish.

BRIEF DESCRIPTION OF THE ILLUSTRATION

The accompanying photograph illustrates the plant in color and shows the flowering thereof from bud to full bloom depicted in color as nearly correct as it is possible to make in a color illustration of this character. Throughout this specification, color values are based upon The Colour Chart of The Royal Horticultural Society of London, England, except where common terms of color definition are employed.

DESCRIPTION OF THE NEW VARIETY

The following description is of rose plants of the new cultivar grown outdoors in October 1993 in Upland, Calif. Phenotypic expression may vary with environmental, cultural and climatic conditions, as well as differences in conditions of light and soil.

FLOWER

The new variety bears its flowers sometimes singly, usually three to four or more per stem. Flowers are borne in irregular rounded clusters on normal strong long stems for the class. Outdoors the plant blooms freely and nearly continuously during the growing season. The flowers have a slight tea to fruity fragrance.

BUD

The peduncle is of short to average length for the class, of average caliper, and usually erect. It is moderately rough, with many stipitate glands, numerous hairs and very small prickles. Peduncle color is between 146A and 144A often suffused with between 183A and 181B.

Before the calyx breaks, the bud is of small to medium size for the class, moderately short in length, and mostly ovoid to somewhat pointed in shape. The surface of the bud is moderately smooth with some stipitate glands and hairs, sometimes with slender entire foliaceous parts extending beyond the tip of the bud equal to $\frac{1}{4}$ or more of its length. Bud color is between 146A and 144A sometimes washed with between 183B and 181C.

The inner surface of the sepals is covered with fine woolly tomentum; sepal margins are lined with few stipitate glands and numerous hairs.

As the first petal opens, the bud is somewhat medium sized for the class, moderately short to medium in length, and somewhat flat-topped to pointed to ovoid in form. Buds measure about 1.4 to about 2 cm in width at the widest point and about 3 to about 4 cm in length. As the first petals open, the size ranges from about 2 to about 2.4 cm at the widest point and about 3.5 to about 4.5 cm in length. The color of the outside surfaces of the newly opened petals is between 15B and 14C sometimes blushed to as deep as between 42B and 45C. The color of the inside surfaces of the newly opened petals is between 42A and 33A irregularly striped with between 15B and 14C. The bud opens up well and is not prevented from opening by wet, cold, hot or dry weather.

BLOOM

When fully open, the bloom is somewhat medium in size for the class, ranging from 9 to 11 cm. in diameter. Petalage is double with 32 to 38 petals and 1 to 4 petaloids arranged irregularly. When partially and fully open, the bloom form is somewhat cupped to full and the petals are moderately cupped to undulated with petal edges moderately rolled outward.

PETALS

The petals are of moderately heavy substance and of medium thickness, with inside surfaces somewhat satiny to velvety and outside surfaces somewhat shiny to satiny. The outer petals are very broadly obovate in shape with apices mostly rounded. The inside petals are less broadly obovate to almost rounded in shape with apices moderately rounded.

NEWLY OPENED FLOWER

The outside surface of the outer, intermediate and inner petals is between 12B and 14D. The inside surface of the outer, intermediate and inner petals is between 33A and 42B irregularly striped with between 12B and 14D. when the petal is dominated by the orange color, a moderately large basal attachment zone of near 13C is evident. There is variation in the striping such that in some flowers stripes of between 12B to 14D predominate and in other flowers stripes of between 33A to 42B predominate. This variation is typical of the new variety.

The general tonality of the newly opened flower is between 33A and 42B irregularly striped with between 12B and 14D.

THREE-DAY-OLD FLOWER

The undersurface of the outer and inner petals is between 10B and 12D. The upper surface of the outer and inner petals is between 33B and 42D irregularly striped with between 12D and 10B. Sometimes the yellow pigmented portion of the upper petal surface will lightly blush with between 33C and 44D. When the petal is dominated by the orange color, a moderately large basal attachment zone of near 11D is evident.

The general tonality of the three-day-old flower is between 33B and 42D irregularly striped with between 12D and 10B.

On the spent bloom, the petals usually drop off cleanly and are not particularly affected by cold, hot, wet, or dry weather.

In October in Upland, Calif., blooms on the bush growing in the garden generally last from four to five or more days. Cut roses grown outdoors and kept at normal indoor living temperatures generally last from four to five days.

MALE REPRODUCTIVE ORGANS

Stamens are average in number and are arranged regularly about the pistil; a few are tucked in the calyx. The filaments are of differing lengths somewhat short to medium, most with anthers. The anthers are moderately small for the class and all open approximately at the same time. Anther color is near 13A when immature and near 163B at maturity. Pollen is moderate in abundant and near 16D in color.

FEMALE REPRODUCTIVE ORGANS

Pistils are average to many in number (approximately 85). The styles are moderately uneven, short to average in length, somewhat thin to average in caliper, and moderately loosely bunched. Stigma color is near 11B. Style color is near 44B. Ovaries are usually all enclosed in the calyx.

Hips are of moderately short length, somewhat ovoid to globular in form, and near 32A in color. The hip surface is very smooth with moderately thick fleshy walls. The sepals fall away soon. Seeds are somewhat few to average in number (approximately 10 to 17), and usually medium in size.

FOLIAGE

The compound leaves are usually comprised of three to seven leaflets and are borne abundantly. The leaves and leaflets are somewhat large for the class, moderately heavy to crips in texture, and moderately glossy in finish. The leaflets are shaped somewhat oval to ovate with moderately acute apices and moderately round bases. Their margins are usually simply serrate. Leaves range from about 11 to about 17 cm in length and about 14 to about 16 cm in width at the widest point. Leaflets range from about 3.5 to about 8 cm in length and about 2.5 to about 6 cm in width at the widest point. By reference to "crisp" in describing the leaves, it is meant that when bent the leaves tend to snap and break as opposed to yielding completely.

The upper surface of the mature leaf is between 146A and 139A sometimes very lightly suffused with near 183A. The undersurface of the mature leaf is between 146C and 191B sometimes lightly suffused with near 183A. The green of the upper and undersurfaces of the young leaf is completely covered by a very heavy suffusion of red-brown tones. The color of the upper surface of the young leaf is between 187A and 183A. The undersurface of the young leaf is near 183A. The dark pigmentation of the new foliage is retained for a moderately long period into the maturation of the leaf.

The rachis is average in caliper and moderately rough with some hairs and stipitate glands on the edges of the upper side. The under side of the rachis is very rough with many hairs, stipitate glands and 2 to 4 very small prickles.

The stipules are medium to long in length with moderately narrow to medium width and somewhat short to medium straight points that sometimes turn out at an angle of about 45 degrees.

The plant displays an above-average degree of resistance to powdery mildew and blackspot as compared to other commercial varieties grown under comparable conditions in Upland, Calif.

GROWTH

The plant has a spreading, medium to tall habit with moderately full branching. The height of the plant ranges from about 180 to about 250 cm with a spread ranging from about 150 to about 170 cm at the widest point. It displays very vigorous growth and the canes are of moderately heavy caliper for the class. Stems of the plant measure about 26 to about 32 cm, peduncles are about 4.5 to about 6 cm.

The color of the major stems is between 146D and 152D. They bear few large prickles which are moderately long for the class. The large prickles are almost straight, curving slightly downward with a medium-length, moderately narrow to rounded base; prickle color is near 166D. The major stem bears several small prickles of similar shape and coloration. There are no coarse hairs.

The color of the branches is between 146A and 139B often somewhat lightly suffused with near 183A. The branches bear few large prickles, which are moderately long for the class. The large prickles are almost straight to curving slightly downward and with a medium-length, moderately narrow to rounded base; prickle color is near 174A. The branches bear many small prickles of similar shape and coloration. There are many coarse hairs of similar coloration.

The color of the new shoots is between 146A and 139B often moderately suffused with near 183A. The new shoots bear several large prickles which are moderately long for the class. The large prickles are almost straight to curving slightly downward with a medium-length, moderately narrow to rounded base; prickle color is between 183A and 187A. The shoots bear many small prickles of similar shape and coloration. There are many coarse hairs of similar coloration.

I claim:

1. A new and distinact variety of shrub rose plant substantially as described and illustrated herein.

* * * * *

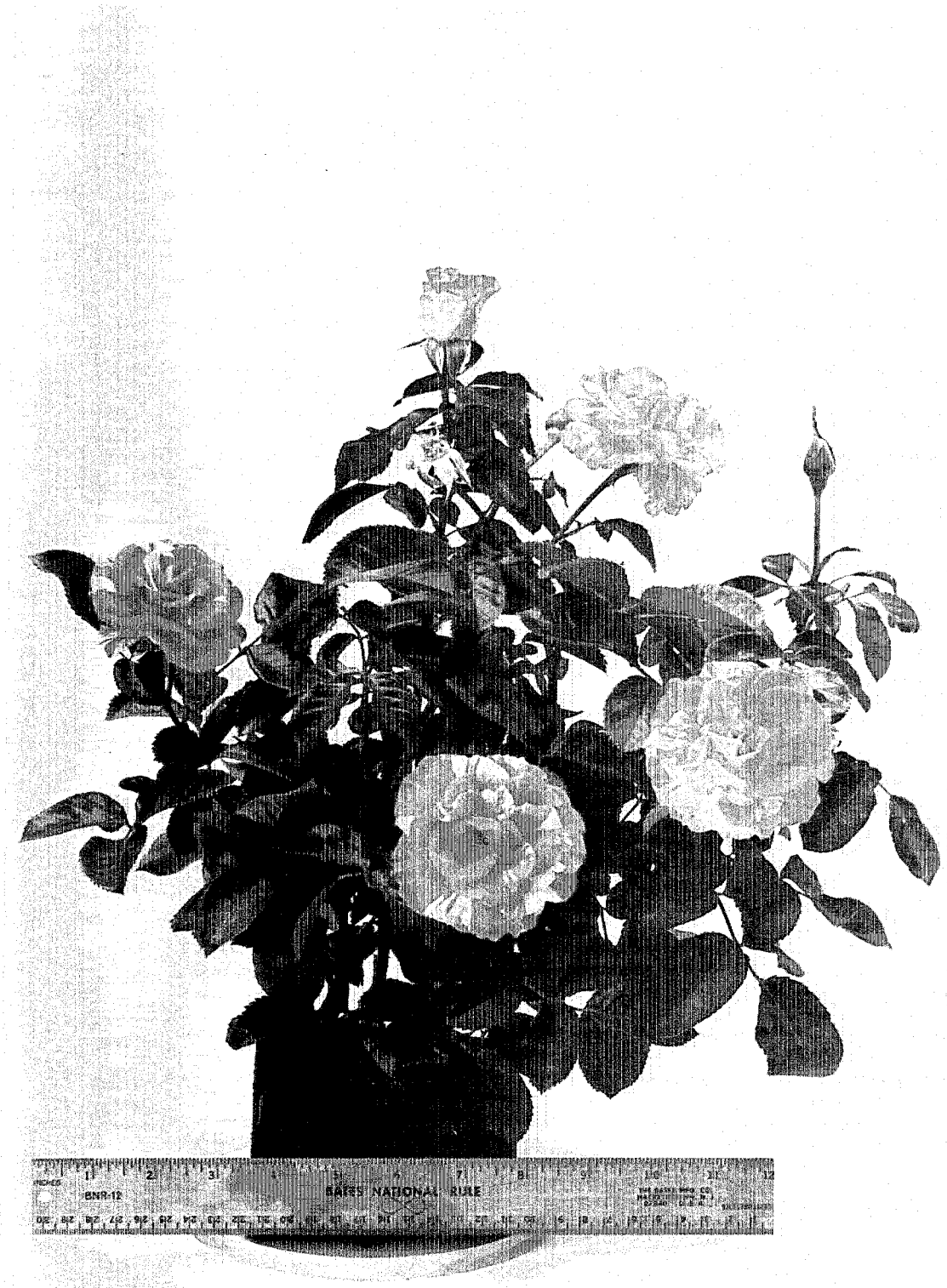
BNR-12
BATES NATIONAL RULE

UNITED STATES PATENT AND TRADEMARK OFFICE

CERTIFICATE OF CORRECTION

PATENT NO. : Plant 9,191

DATED : July 11, 1995

INVENTOR(S) : Sam McGredy

It is certified that error appears in the above-indentified patent and that said Letters Patent is hereby corrected as shown below:

On the title page, [54] Title, change "NAMES" to -- NAMED --.

Column 4, line 9, after "moderate" change "in" to -- to --.

Column 4, line 30, change "crips" to -- crisp --.
Column 6, line 17, change "distinact" to -- distinct --.

Signed and Sealed this

Fifth Day of December, 1995

*Attest:*

*Attesting Officer*

Bruce Lehman

BRUCE LEHMAN

*Commissioner of Patents and Trademarks*